United States Patent [19]

Hamid

[11] 4,106,340

[45] Aug. 15, 1978

[54] GRADING AGRICULTURAL PRODUCTS WITH A MICROWAVE ANTENNA

[75] Inventor: Michael A. Hamid, Winnipeg, Canada

[73] Assignee: Her Majesty the Queen in right of Canada, as represented by the Minister of National Defence, Ottawa, Canada

[21] Appl. No.: 728,651

[22] Filed: Oct. 1, 1976

[30] Foreign Application Priority Data

Apr. 7, 1976 [CA] Canada ................................. 249712

[51] Int. Cl.² ........................... G01J 5/46; H04B 7/00
[52] U.S. Cl. ................................................ 73/355 R
[58] Field of Search ........... 73/15 R, 355 CM, 355 R; 209/111.5; 250/336; 325/363; 343/100 ME

[56] References Cited

U.S. PATENT DOCUMENTS

| | | | |
|---|---|---|---|
| 3,028,596 | 4/1962 | McGillem et al. | 73/355 |
| 3,129,330 | 4/1964 | Seling | 343/100 |
| 3,373,869 | 3/1968 | Burson, Jr. | 209/111.5 X |
| 3,451,254 | 6/1969 | Maley | 73/355 X |
| 3,911,435 | 10/1975 | Mardon et al. | 73/355 |

Primary Examiner—Herbert Goldstein
Attorney, Agent, or Firm—Sughrue, Rothwell, Mion, Zinn and Macpeak

[57] ABSTRACT

A method and apparatus for continuous and contactless grading and counting in which the articles or products to be surveyed are passed beneath a microwave radiometer antenna on a conveyor belt or the like, so as to measure the frequency spectrum of the radiation temperature emitted by the articles at a convenient temperature and relating the "signature" thus obtained to a non-electrical parameter such as weight or size.

5 Claims, 5 Drawing Figures

GRADING AGRICULTURAL PRODUCTS WITH A MICROWAVE ANTENNA

This invention relates to continuous and contactless grading and counting of products passing along a conveyor belt or the like. More particularly this invention relates to the continuous and contactless grading and counting of agricultural products, such as eggs, tomatoes and the like by microwave radiometric assessment of the frequency spectrum of the radiation temperature emitted by the products, and relating this assessment to a non-electrical parameter such as weight or volume.

Continuous and semi-continuous counting and grading techniques have developed considerably in the past few years and are widely applied in many industries to separate products into different catagories according to volume, weight or quality. Such techniques include on-line manual inspection, direct measurement of weight or volume, measurement of linear dimensions by light sensitive detectors and measurement of surface characteristics such as color, roughness and the like by various light sensitive detectors. All such techniques have their place in industry and, depending upon the speed required, are more or less successful. There is, however, a continuing need for new and more sophisticated sorting and grading techniques which will be accurate and reliable at the processing and packaging speeds now contemplated on certain high speed production and packaging lines. This need is particularly acute in the field of food processing and packaging, where rapid and accurate sorting for size and quality of produce at minimum cost is required.

It is an object, therefore of the present invention to provide a relatively inexpensive method for rapid, continuous and contactless grading and counting of articles, particularly agricultural produce by microwave radiometric means.

Thus by one aspect of this invention there is provided a method for contactless grading a plurality of objects, comprising:

(a) scanning a selected said object with a microwave radiometric antenna means at a series of frequencies in the range 12-18 GHz and measuring radiometric output intensity from said object to thereby establish an optimum frequency corresponding to maximum radiometric output;

(b) sequentially bringing a plurality of said objects into close proximity with said antenna means and effecting relative movement therebetween so as to scan each of said objects;

(c) measuring the radiometric output intensity for each said object at said optimum frequency to thereby establish a signature for each said object; and (d) relating each said signature to a preselected non-electric parameter of said object and thereby effecting grading of said objects.

By another aspect of this invention there is provided apparatus for contactless grading and counting a plurality of objects comprising:

(a) a microwave radiometer having antenna means for sequential scanning of each said object;

(b) means to convey said objects into close proximity with said antenna means for scanning thereby;

(c) means to measure radiation intensity, at a selected frequency in the range 12-18 GHz, of the radiation emission of said objects, thereby establishing a signature for each said object; and (d) means to compare said signature with a preselected non-electric parameter of said object.

The invention will be described in more detail hereinafter with reference to the accompanying drawings in which.

As previously indicated the principle upon which the present invention is based is the measurement of the frequency spectrum of the radiation temperature emitted by the object of interest, such as eggs, apples, oranges, onions, or manufactures such as nuts, bolts, screws or rods, at a convenient temperature. Normally room temperature is selected as corresponding to the usual condition prior to storage or shipping. The frequency spectrum, which is proportional to the change in the apparent temperature of the background, is measured as a function of voltage for each individual frequency selected, and thus generates a unique signature which can be directly related to a non-electrical parameter of interest. To a first approximation it has been found that the signature at a single frequency is linearly related to the selected non-electrical parameter as long as the object size remains within a preselected range. Since this range generally corresponds to the usual dimensions encountered in practice, an inversion procedure to establish quantitative information on such parameters as diameter and length or qualitative information such as grade or ripeness about the article or product under examination can be set up and displayed by graphical or digital display or set to actuate a selection device such as an on-line electro-pneumatic grading system, known per se. Generally, the frequency to be employed is selected by frequency scanning through the 12-18 GHz ($K_u$) band and selecting the frequency corresponding to the best radiometric sensitivity.

It will also be appreciated that the articles under examination are generally carried on a moving conveyor which moves under a fixed radiometer antenna, operating at a selected frequency, so that the articles are only visible to the antenna for a relatively short time period, depending on the size of the article and the speed of the conveyor. In the alternative the antenna means may be moved relative to a fixed article. The signals received by the antenna amount to an intermittent perturbation in the background signature and can therefore be counted as pulses representative of the number of articles passing per unit time. Thus the frequency of pulses provides the counting rate while the height or amplitude of each pulse is related to the average radiation temperature of the article and by analogy with the average dielectric constant which also depends on the individual properties of the shell and core composition. The amplitude provides information about either the article size (volume or weight) assuming the basic composition remains the same or the composition (ripeness, age, physical temperature, color, etc.) assuming that the object size remains the same, but clearly not both.

Figure 1:
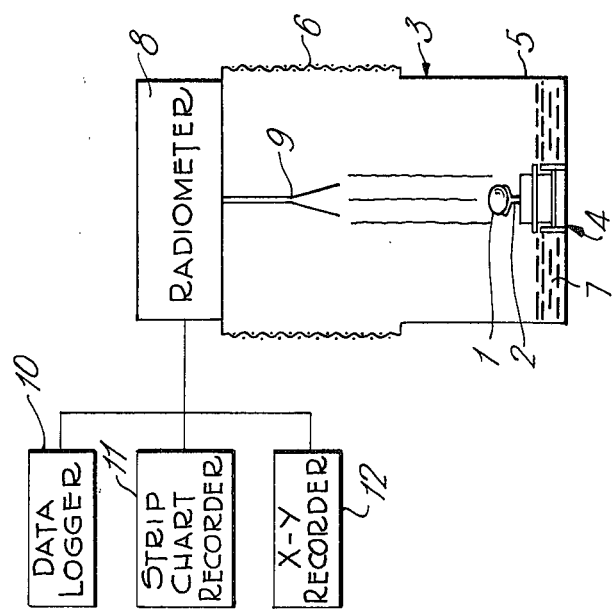
FIG. 1 is a schematic view of a scanning apparatus according to the present invention.

One form of an apparatus for scanning samples according to the present invention is shown diagrammatically in FIG. 1. A sample 1 on a suitable support 2 is carried through a sampling station indicated generally at 3 on a conveyor 4. The station 3 is contained within a tank 5 having screened sides 6 and a water layer 7 on the bottom thereof. A microwave Dicke-type radiometer 8 operating in the 12-18 GHz band ($K_u$ band) is mounted above the conveyor and provided with an antenna $K_u$ band pyramidal horn 9 oriented to receive a signal from the sample 1. The radiometer is operatively connected to appropriate recorders 10, 11 and 12 in known fashion. The circuitry for the radiometer is shown schematically in FIG. 2. For classification purposes, the $K_u$ band (12-18 GHz) Dicke type radiometer system is subdivided into three main sections: the antenna section, the radio frequency (R.F.) section and the intermediate frequency (I.F.) section which includes the audio output.

Antenna Section

This consists of pyramidal horn antenna 9 located at a distance of 7.75 inches above the sample which was supported on an aluminum support 2. The antenna aperture dimensions are conveniently 6 × 5 inches with the larger dimension parallel to the longer dimension of the feed waveguide, and its axial height or distance from throat to midpoint of aperture is 12.75 inches. The antenna supplies the R.F. input signal which is the signature of the sample object. Also included in this section is a slide screw tuner (for example, Hewlett-Packard model P870A) for antenna impedance matching, noise source (for example, a Waveline model 2200-7 argon gas tube), attenuator (for example, a Waveline model 703), reference load termination (for example, a Waveline model 754) and power supply (for example, a Waveline model 2200, ser. U727).

R.F. Section

This section consists of:

1. a waveguide circulator switch (for example, an E & M model $K_u$ 134 LYS) with driver (for example, an E & M model EDS 1.5A);
2. 16.9 dB gain and 5.6 dB noise figure tunnel diode amplifier (for example, an Aertech model 8740A) followed by a 42 dB gain and 11.5 dB noise figure travelling wave tube amplifier (for example, a Varian model VTU 4390B1);
3. $K_u$ band mixer (for example, a Spacekom model CKU-3); and
4. $K_u$ band local oscillator (for example, a Varian Klystron model VA 94B).

The resulting overall R.F. system gain was optimized at 58.9dB.

I.F. Section

This section is a self-contained solid state high sensitivity receiver packaged and sold commercially as Spacekom Radiometer Receiver model UHF-6R with audio output terminals for signature tracing on an $x$–$y$ recorder as indicated in FIG. 1. This system may be operated in the continuous signal mode or the switched mode of operation. For the switched mode of operation, a suitable frequency timing wave is internally generated to operate the synchronous detector and also for use as a control signal for the R.F. antenna reference switch. The I.F. bandwidth is 180 MHz with provisions for use of plug-in filters to restrict the bandwidth as desired. The overall gain is nominally 85 dB with a nominal I.F. noise figure of 2 dB.

EXAMPLE 1

Figure 2:
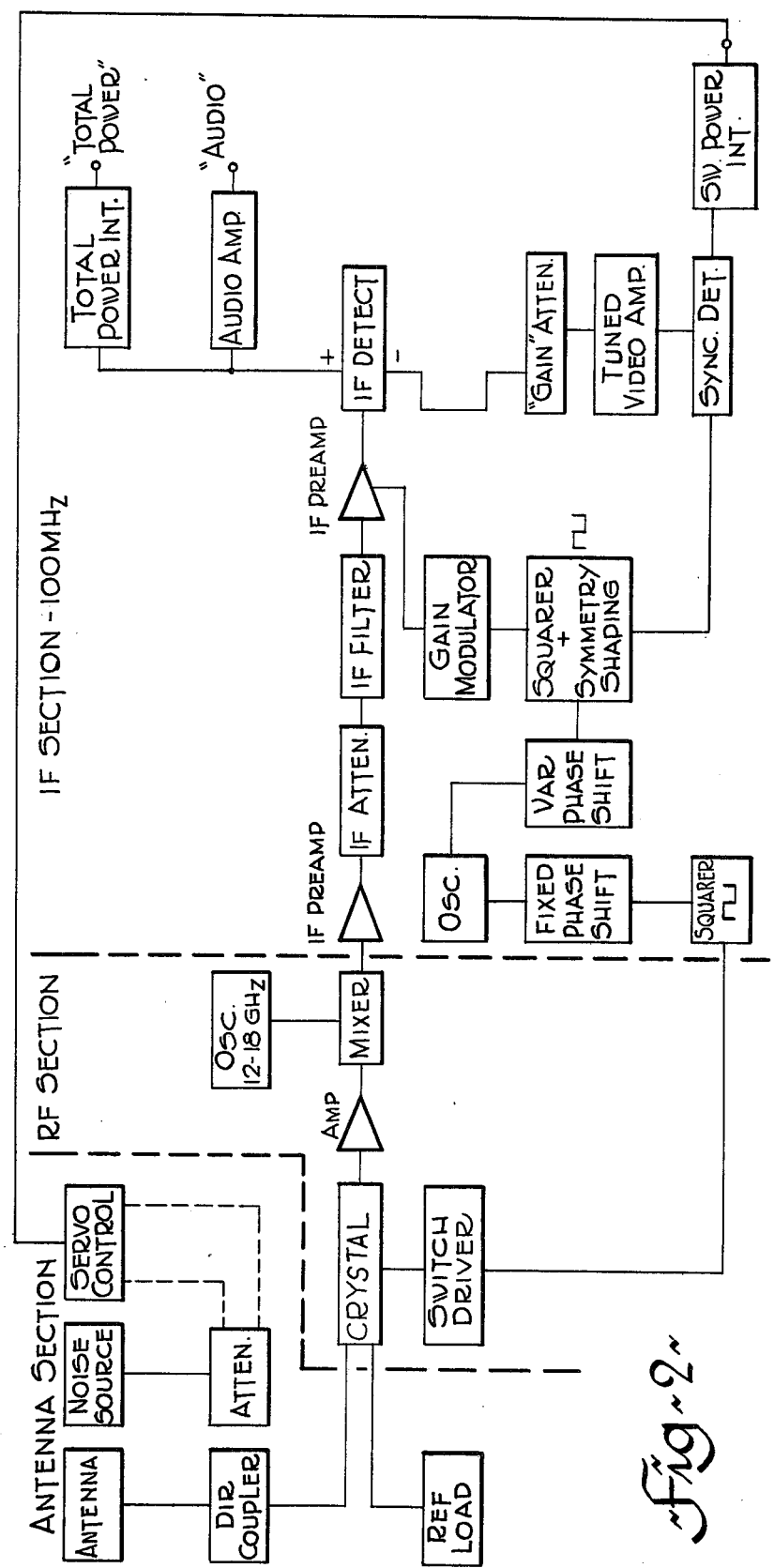
FIG. 2 is a block diagram of a multifrequency microwave radiometer suitable for use in the apparatus of FIG. 1.

Egg samples of the size set forth in Table 1 were scanned, on an apparatus as described with reference to FIGS. 1 and 2, in both the small-end down and sideways position with the radiometer set at 14.32GHz operating frequency, 180MHz IF bandwidth and 1 second integration time.

Table 1

| Egg Sample | Volume (ml) | Weight (gm) |
|---|---|---|
| Small | 48 | 49.60 |
| Medium | 55 | 55.68 |
| Large | 57 | 59.66 |
| Extra Large | 68 | 70.60 |

Figure 3:
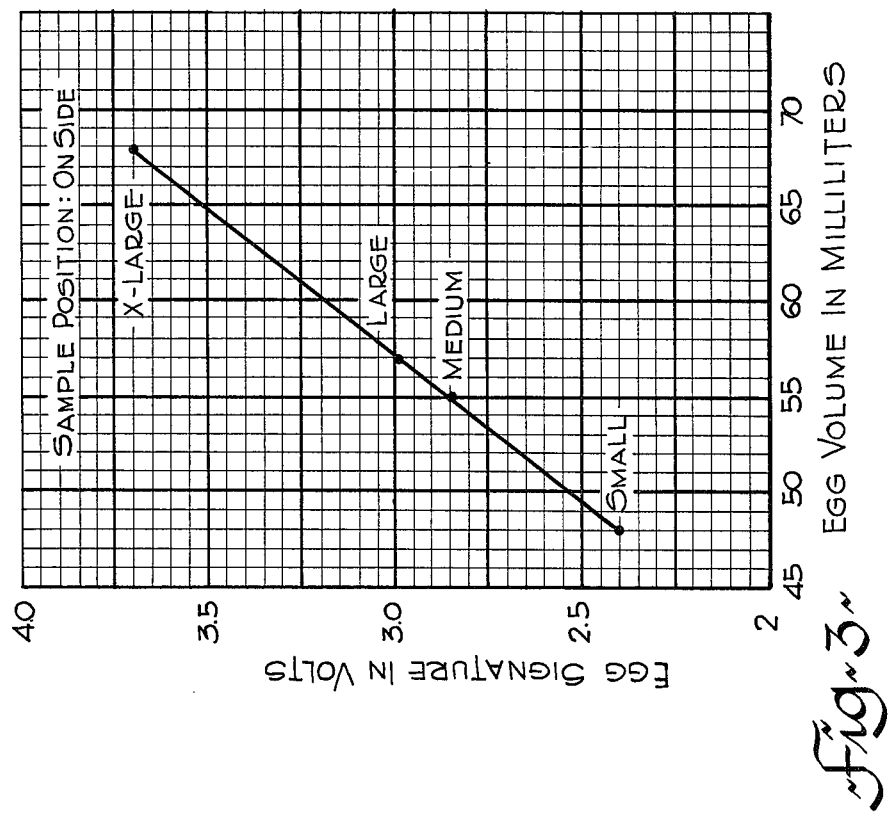
FIG. 3 is a graph showing the relationship between egg volume and recorded electrical voltage for eggs positioned on their side, and is located on the sheet containing FIG. 1.
Figure 4:
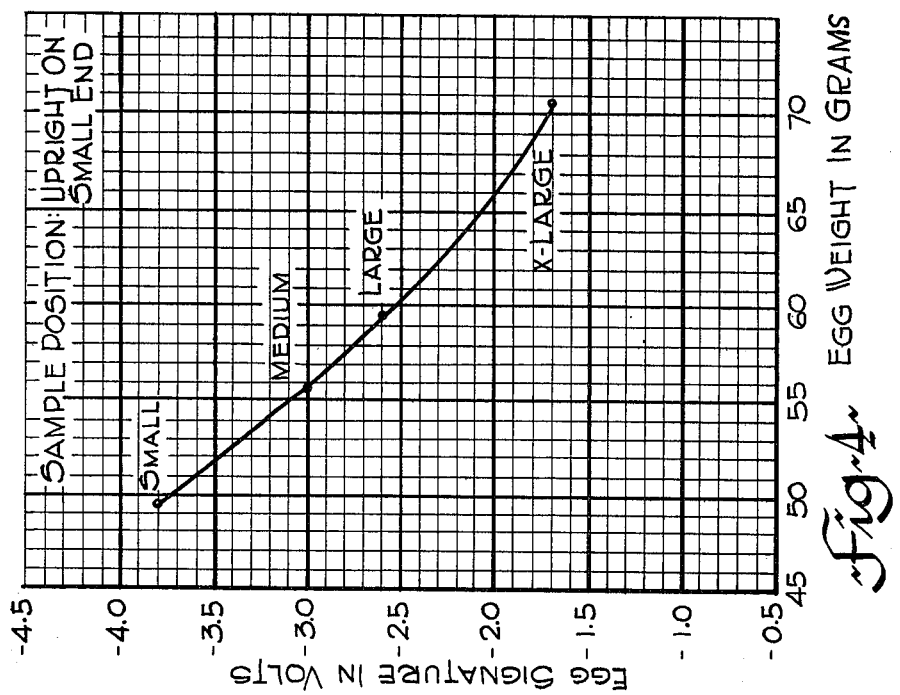
FIG. 4 is a graph showing the relationship between egg weight and recorded electrical voltage for eggs positioned small end down.

The results are shown in FIGS. 3 and 4. FIG. 3 shows the relationship between egg volume and signature voltage for eggs placed on their sides and FIG. 4 shows the relationship between egg weight and signature voltage for eggs placed in the small end down position. FIG. 3 indicates that a linear relationship is obtained for an object having substantial rotational symmetry. For an object having no rotational symmetry, as with an egg in the end on position, the degree of accuracy or linearity decreases proportionally as is shown in FIG. 4. This is believed due to the masking effect of the lower layers or lower part of the body by the upper part and the polarization of the antenna on the position.

EXAMPLE 2

Figure 5:
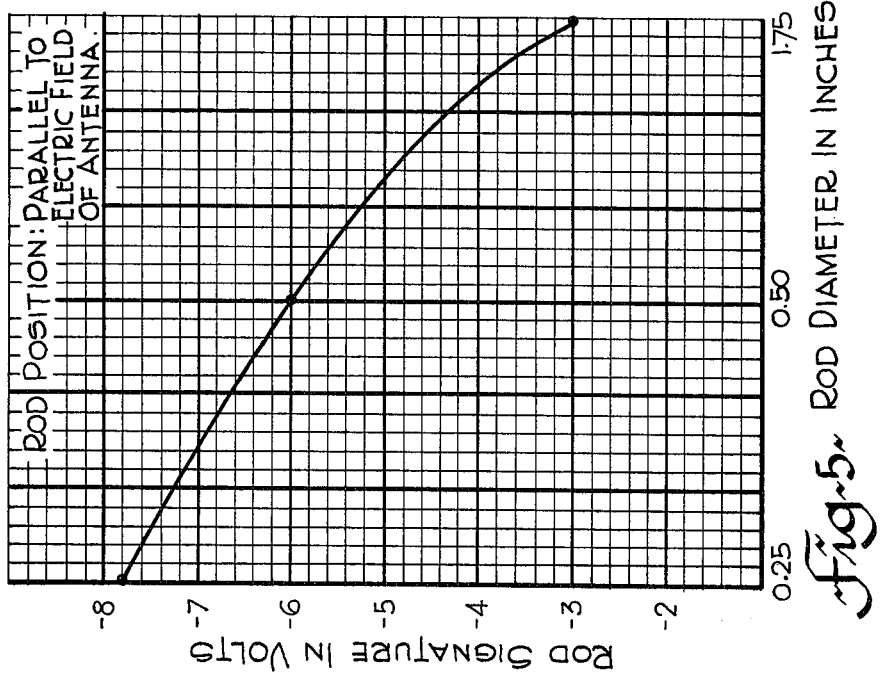
FIG. 5 is a graph showing the relationship between brass rod diameter and recorded electrical voltage.

Brass rod samples 0.75 inch, 0.5 inch and 0.25 inch diameter with a constant length of 7 inches were scanned in a microwave radiometer device as described with reference to FIGS. 1 and 2 and following a similar technique as outlined in Example 1. The horn to rod separation was maintained at 1 inch with the radiometer settings as in Example 1 and with the electric field vector of the antenna parallel to the cylindrical axis of the rod samples. The results are illustrated diagrammatically in FIG. 5 which shows, in the preferred rod position parallel to the electric field, that there is a substantially linear relation between the signature and the size, but that the linearity is still restricted to the perturbation range. Although FIG. 5 shows the frequency spectrum at room temperature it will be appreciated that this technique could advantageously be applied to the output from a hot rolling mill, where the radiation emission temperature will be much higher and the equipment more sensitive. It will be appreciated that the principles of the present invention may be applied to many grading and counting problems without departing from the scope of this invention which is defined only by the appended claims. For example many articles other than eggs and brass rods may be scanned and other parameters in eggs and the like may be calibrated. For example, the system, when coupled to an on-line electropneumatic grading and gating system, would not only provide an accurate numerical count but also separate graded eggs into different gates according to color, shell thickness, size of yolk, presence of blood spots and air pockets, age, etc.

I claim:

1. A method for contactless grading a plurality of objects, comprising:
    (a) scanning a selected said object with a microwave radiometric antenna means at a series of frequencies in the range 12–18 GHz and measuring radiometric output intensity from said object to thereby establish an optimum frequency corresponding to maximum radiometric output;
    (b) sequentially bringing a plurality of said objects into close proximity with said antenna means and effecting relative movement therebetween so as to scan each of said objects;
    (c) measuring the radiometric output intensity for each said object at said optimum frequency to thereby establish a signature for each said object; and
    (d) relating said signatures to a preselected non-electric parameter of said object whereby said objects may be graded by comparing their respective signatures to a standard established for that parameter.

2. A method as claimed in claim 1 wherein said objects are selected from similarly sized agricultural products and similarly sized manufactured products.

3. A method as claimed in claim 1 wherein said objects are carried on a continuously moving conveyor means in spaced relationship to said antenna means.

4. A method as claimed in claim 1 wherein said objects are scanned at room temperature.

5. Apparatus for use in contactless grading a plurality of objects comprising:
    (a) a microwave radiometer having antenna means for sequential scanning of each said object;
    (b) means to convey said objects into close proximity with said antenna means for scanning thereby;
    (c) means to measure radiation intensity, at a selected frequency in the range 12–18 GHz, of the radiation emission of said objects, which defines a signature for each said object whereby objects may be graded by comparison of their respective signatures to a standard co-related to a non-electrical preselected parameter of said objects.

* * * * *